United States Patent [19]
Fournier

[11] Patent Number: 6,023,985
[45] Date of Patent: Feb. 15, 2000

[54] CONTROLLER FOR AN ENVIRONMENTAL TEST CHAMBER

[75] Inventor: Michael T. Fournier, Fort Collins, Colo.

[73] Assignee: Hewlett-Packard Company, Palo Alto, Calif.

[21] Appl. No.: 09/039,892

[22] Filed: Mar. 16, 1998

[51] Int. Cl.$^7$ .................................................. G01N 25/00
[52] U.S. Cl. ............................................................ 73/865.6
[58] Field of Search .................................... 73/159, 865.6, 73/865.8, 865.9; 374/57; 219/401; 236/44 R, 44 A, 44 C, 47

[56] References Cited

U.S. PATENT DOCUMENTS

| | | | |
|---|---|---|---|
| 3,488,681 | 1/1970 | Mita et al. | 73/865.6 |
| 4,602,503 | 7/1986 | Hile et al. | 73/865.6 |
| 4,667,522 | 5/1987 | Kawahara | 73/865.6 |
| 4,957,011 | 9/1990 | Huber et al. | 73/865.6 |
| 5,469,707 | 11/1995 | Dadachanji | 62/3.3 |
| 5,631,429 | 5/1997 | Cutright et al. | 73/865.6 |
| 5,660,103 | 8/1997 | Koopman | 99/468 |

*Primary Examiner*—Robert Raevis

[57] ABSTRACT

An apparatus for performing environmental testing on a device, and a method for controlling the atmospheric conditions of the apparatus are disclosed. The apparatus includes a test chamber and at least one air heater for controlling air temperature within the test chamber. The apparatus further includes at least one liquid heater for disposed in connection with a liquid reservoir for heating the liquid to control humidity within the test chamber. Finally, the apparatus includes first and second controllers for controlling the at least one air heater and the at least one liquid heater, and thus for controlling the temperature and humidity within the test chamber. In accordance with the method, the method includes the steps of beginning a testing cycle at a first temperature and a first humidity, and first elevating the temperature of a test chamber to at least a second temperature (where the second temperature is higher than the first temperature), while maintaining the humidity at a substantially constant level. Then, the method holds the temperature in the test chamber at a near constant temperature for a period of time. Finally, after the temperature has been elevated to its desired (target) temperature, the method elevates the humidity in the test chamber from the first humidity to at least a second humidity (where the second humidity is higher than the first humidity), while holding the temperature at a substantially constant value.

12 Claims, 4 Drawing Sheets

CONTROLLER FOR AN ENVIRONMENTAL TEST CHAMBER

BACKGROUND OF INVENTION

1. Field of the Invention

The present invention generally relates to environmental test systems, and more particularly to an improved controller for controlling the environmental conditions within a test chamber of an environmental test apparatus.

2. Discussion of the Related Art

As is known, many applications for PC boards involve hostile operating environments, particularly including temperature extremes and sometimes, rapid excursions between such extremes. The operating environment may also include vibration which must be withstood by the PC boards. Unless recognized in board construction and testing, such environments can cause premature failure of the board per se and/or of the components mounted thereon.

To help assure that PC boards provide the requisite degree of reliability in such applications, board manufacturers often subject them to temperature tests (often referred to as "stress tests" or "stress screening") by placing them in an environmental test chamber capable of producing rapid and extreme changes in temperature. For example, such a chamber might provide a temperature change of from 40° F. to over 200° F. in about 30 minutes. The stress test may also include vibrating the PC boards being subjected to such temperature extremes. Stress screening pulls out PC boards that exhibit what is often called "infant mortality"—i.e., boards which fail prematurely under the rigors of such screening.

In addition to temperature and stress testing, those who make PC boards have sometimes been required to impose yet an additional form of stress—that of changing humidity. An example of an application for PC boards subjected to the additional rigors of humidity testing is aircraft electronic systems. Both commercial and military aircraft can be exposed to both very dry ambient air and very humid ambient air in a relatively short time.

Until the advent of the invention, those who test PC boards by stress screening had three choices, none of which were particularly attractive from an economic standpoint. One choice was to anticipate the need for humidity testing by purchasing (at added cost) an environmental test chamber configured with a humidity-changing capability. But relatively few PC boards are required to be tested under controlled humidity conditions since the humidity-related components may be underutilized or not used at all.

Accordingly, many environmental testing devices of the prior art define either a temperature testing chamber or a humidity testing chamber. Indeed, U.S. Pat. No. 5,631,429 (the '429 patent) characterizes a shortcoming of prior art testing systems as requiring separate testing apparatus for performing temperature testing and humidity testing. Accordingly, the '429 patent discloses an environmental testing apparatus and method that allows and performs both types of testing in a single apparatus. However, as contemplated therein, the temperature testing and humidity testing are to be performed at different times, often spaced apart by several months (see col. 2, line 57). Indeed, a separate "humidity module" must be installed in that device when humidity testing is desired.

One shortcoming of prior art systems relates to condensation build-up. Indeed, the '429 patent notes the significance of a drain conduit that is used to remove any condensation forming in the chamber, during temperature testing (the conduit has a different purpose during humidity testing). High levels of condensation within a test chamber can result in increased incidence of component failure, particularly when testing sensitive electronic equipment, such as integrated circuit components.

Accordingly, what is desired is an improved environmental test system that accommodates simultaneous temperature and humidity testing, and which provides improved condensation control.

SUMMARY OF INVENTION

Certain objects, advantages and novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the advantages and novel features, the present invention is generally directed to an apparatus for performing environmental testing on a device, and a method for controlling the atmospheric conditions of the apparatus. In accordance with one aspect of the invention, the apparatus includes a test chamber and at least one air heater for controlling air temperature within the test chamber. The apparatus further includes at least one liquid heater for disposed in connection with a liquid reservoir for heating the liquid to control humidity within the test chamber. Finally, the device includes first and second controllers for controlling the at least one air heater and the at least one liquid heater, and thus for controlling the temperature and humidity within the test chamber.

Preferably, the system includes a computer that provides centralized control over all controllers, wherein the computer controls the first controller to elevate the temperature within the test chamber, while holding the humidity at a substantially constant level. After the chamber temperature has been elevated, then the computer controls the second controller to elevate the humidity within the test chamber. This ordered approach to the testing process minimizes the formation and accumulation of condensation within the test chamber.

In accordance with another aspect of the invention, a method is provided for controlling the atmospheric conditions within an environmental test chamber so as to minimize the formation and accumulation of condensation within the test chamber. In accordance with the preferred embodiment, the inventive method includes the steps of beginning a testing cycle at a first temperature and a first humidity, and first elevating the temperature of a test chamber to at least a second temperature (where the second temperature is higher than the first temperature), while maintaining the humidity at a substantially constant level. Then, the method holds the temperature in the test chamber at a near constant temperature for a period of time. Finally, after the temperature has been elevated to its desired (target) temperature, the method elevates the humidity in the test chamber from the first humidity to at least a second humidity (where the second humidity is higher than the first humidity), while holding the temperature at a substantially constant value.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE PREFERRED EMBODIMENT

Figure 1:
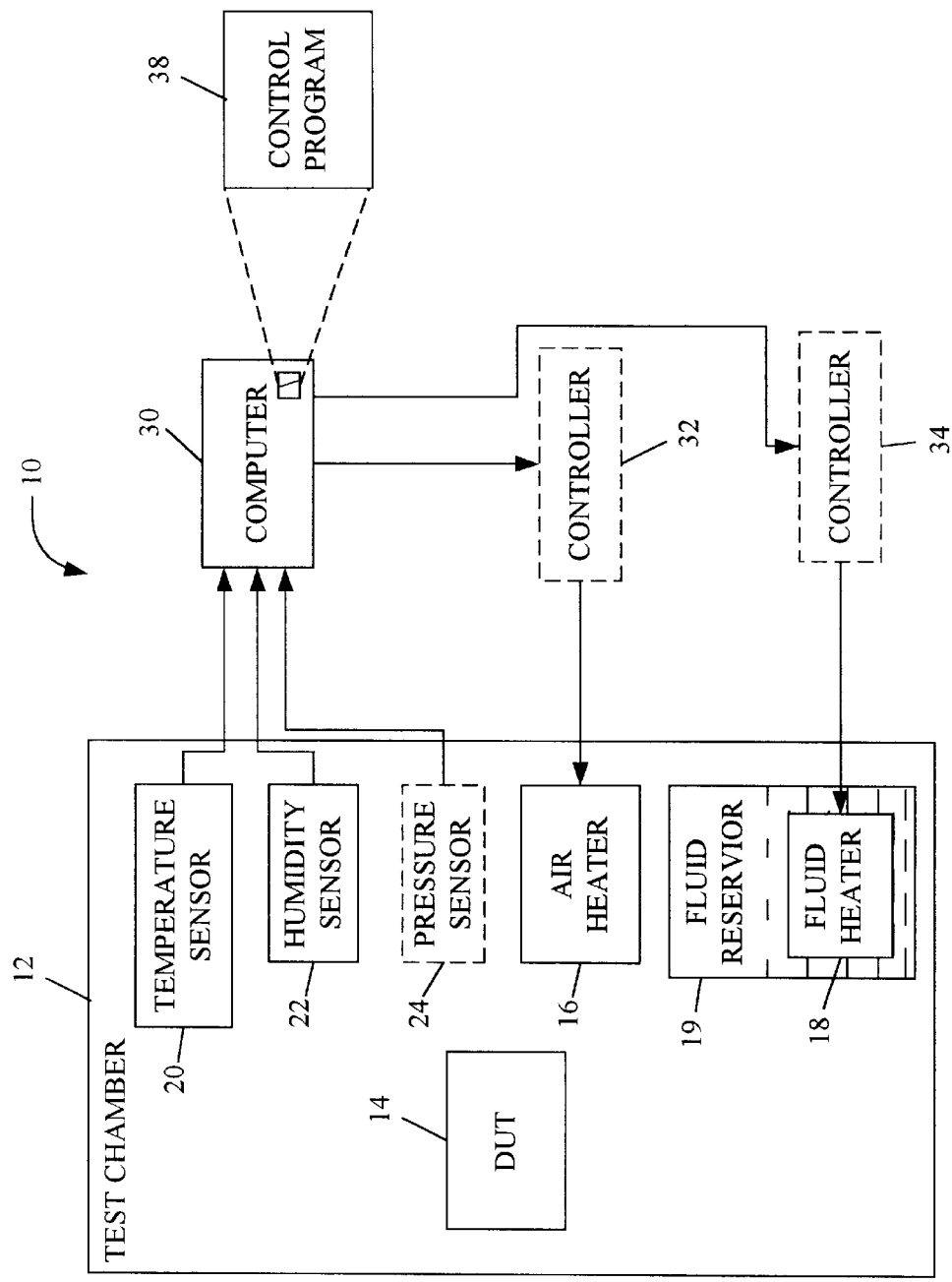
FIG. 1 is a block diagram of an environmental test chamber and controller, constructed in accordance with one aspect of the present invention.

Having summarized the invention above, reference will now be made in detail to the description of the invention as illustrated in the drawings. While the invention will be described in connection with these drawings, there is no intent to limit the invention to the embodiment or embodiments disclosed therein. On the contrary, the intent is to cover all alternatives, modifications and equivalents included within the spirit and scope of the invention as defined by the appended claims.

Turning now to the drawings, reference is made to FIG. 1, which is a block diagram that shows an apparatus for conducting environmental testing of a device under test, generally designated by reference 10. The testing apparatus is of the type having a test chamber 12 that defines a sealed volume of space having controllable atmospheric conditions. More specifically, and as is known, the test chamber 12 is a chamber wherein a device under test 14 may be placed and subject to environmental testing. Typically, environmental testing includes temperature testing, humidity testing, pressure testing, etc. For controlling these conditions, an air heater 16 is disposed within the confined space of the test chamber 12, and may be controlled by an outside controller 32 for controlling the heated temperature within the test chamber 12. As a part of this control, a temperature sensor 20 is typically disposed within the test chamber 12 to provide feedback for a computer 30, for example, which in turn controls the operation of the controller 32.

In similar fashion, the humidity of the test chamber 12 may be controlled by controlling the operation of a fluid heater disposed within a fluid reservoir 19. Generally, the fluid reservoir 19 is simply a container of water or some other fluid that may be heated by the fluid heater 18. As the temperature of the fluid within the fluid reservoir 19 exceeds its vaporization temperature, water vapor is released into the test chamber 12, thereby elevating the humidity (and pressure) therein. Like the air temperature control, a humidity sensor 22 is disposed within the test chamber 12 to provide feedback to the computer 30, which in turn controls the operation of the controller 34. Thus, it is contemplated that both temperature and humidity control are closed-loop control systems operating under the centralized control of a computer 30.

Typically the pressure within the test chamber 12 is simply a function of the temperature and humidity within the chamber. A pressure sensor 24, however, may be disposed within the test chamber 12 to provide a pressure signal to the computer 30, for use when a pressure variable is necessary or desired for the control equations of the control program for controllers 32 and 34. As it is understood by those skilled in the art, the specific control program 38 may vary depending upon the device under test 14 as well as the specifications for the test to be conducted thereon. Commonly, the controller will be implemented as a PID (Proportional-Integral-Derivative) controller. For example, under certain, relevantly simple testing procedures, the testing specifications may simply require that the air temperature of the test chamber 12 be elevated to a certain pre-defined temperature, then held at that temperature for a certain period of time. Alternatively, the testing specifications may define the rate at which the temperature is to increase within the test chamber 12. Certainly, and as will be appreciated by those skilled in the art, as the testing specification or procedure becomes more complex, the control program 38 will become correspondingly more significant.

Since the various testing specifications for different devices 14 may vary greatly, the specifics of any given testing procedure will not be described herein. Indeed, the specifics of such a control program 38 may be readily obtained by persons of ordinary skills in the art, in light of the inventive concepts described herein. In short, the present invention operates to control and coordinate the elevation of the temperature within the chamber 12 as well as the humidity and pressure within the chamber 12, so as to minimize any condensation that may develop within the chamber or on the device under test 14.

Figure 2:
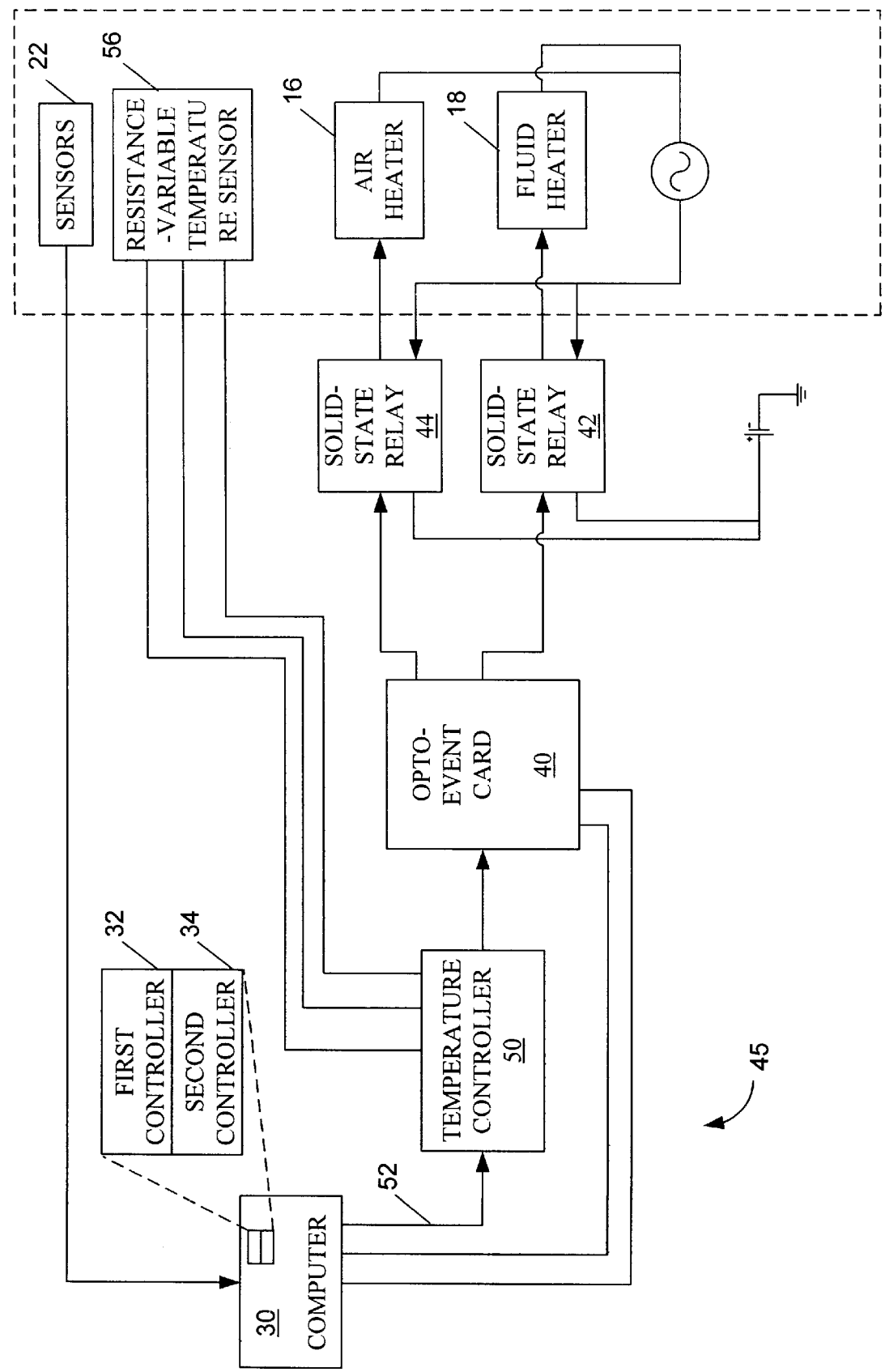
FIG. 2 is a block diagram of an environmental test chamber and controller, constructed in accordance with a preferred embodiment of the invention.

Reference is now made to FIG. 2 which shows a block diagram of the hardware used to implement the control system of a preferred embodiment of the present invention. As illustrated, a central computer 30, such as a high-performance microprocessor-based computer, is configured to provide centralized control of the atmosphere and environmental conditions inside the test chamber 12. Within the computer 30, a first controller 32 and second controller 34 are provided. In this regard, the controllers 32 and 34 are preferably implemented in software, which may be loaded on the computer 30 and configured as necessary to control the testing procedure. In this regard, the computer 30 may be a desktop or laptop computer running a control program having a user interface that permits a user to configure the testing apparatus 10 in order to specify a particular test to be run. The program executed by the computer 30 may pre-define a number of test procedures that may be, for example, selected from a list. Alternatively, the program may also allow the user to specify testing conditions and parameters to be carried out by the computer 30 and controllers 32 and 34. The heaters 16 and 18 that are disposed within the test chamber 12 are controlled by a control card 40 (circuit card). In the preferred embodiment, the control card 40 is implemented as opto-event card having outputs for controlling solid state relays 42 and 44. Through the these relays 42 and 44, the controller 40 operates to either turn heaters 16 and 18 on or off. Of course, the on-off duties cycles of the heaters 16 and 18 define the rate of elevation of the air temperature and humidity, respectively, within the test chamber 12. The control card 40 or its equivalent may take a variety of forms, consistent with the inventive concepts of the present invention.

In the preferred embodiment, the opto-event card is the OPTO 22 card, and it is utilized to control seven input relays and eight output relays. The input relays receive signals from device (e.g., sensors) within the test chamber or from the chamber unit, and the output relays control devices within the test chamber. For example, a fluid sensor, that senses a fill state of the reservoir 19 may generate an input to an input relay. In response, an output relay may be used to control (e.g., shut off) a solenoid that controls the fluid fill of the reservoir.

Event lines 45 are input into the control card 40. In a preferred embodiment, the computer 30 utilized is a Pentium-based microprocessor computer. A plurality of digital event lines are out 45 are outputs from the Pentium processor and directed to the opto event card, to control the relays thereon. In the preferred embodiment, the DIO card manufactured by National Semiconductor is used as the control card 40. A logic zero on a line may be used to turn off a relay, while a logic one may turn on a relay.

In accordance with the preferred embodiment of the invention, a dual-channel temperature controller 50 is also provided, having an independent channel for controlling each of the heaters 16 and 18. In the preferred embodiment, the temperature controller 50 utilized is the model 998 temperature controller manufactured by Watlow. Specifications for this device may be obtained from the manufacturer or other sources, and need not be described herein.

One control input for the temperature controller 50 is provided by way of the serial communication line 52 of the computer 30, which communicates test information pertaining to the control of both channels of the controller 50. Another input to the temperature controller 50 is provided from temperature sensor 56. The temperature sensor 56 of the preferred embodiment is a resistance-variable temperature sensor, defined by a resistance that is variable (as the name implies) in response to temperature (much like a thermistor).

Figure 3:
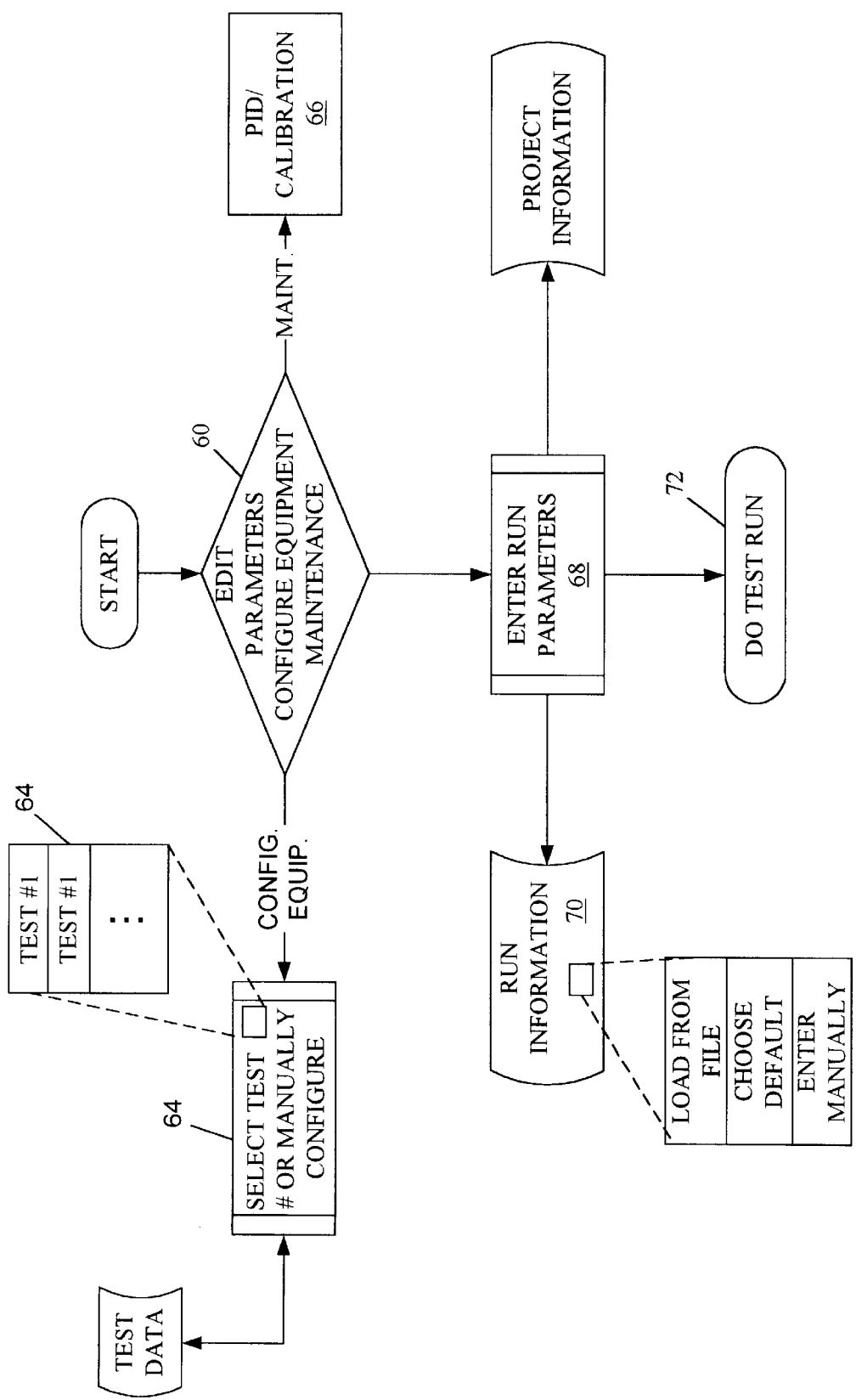
FIG. 3 is a flowchart illustrating the configuration and operation of an environmental test chamber constructed in accordance with the invention.

To illustrate the operation of the preferred embodiment of the present invention, reference is now made to FIG. 3, which is a flow chart that illustrates the user interface of the present invention. In this regard, at the "main menu" level of the program operation a user may select one of several options that will allow the user to configure the equipment, edit and run parameters, or perform certain program maintenance. If the user elects to configure the equipment, then a program routine is entered that allows a user to select a test for execution, which may be selected from a list of pre-defined tests 62, or alternatively to manually configure or define a test specification (64). If the user elects to perform system maintenance, various programs may be modified by the user. For example, the system may be out for calibration of the PID controllers (discussed previously), at step 66. Alternatively, the user may select and edit run parameters option. From this option (step 68) the user may, for example, enter run information (step 70), which may be loaded from a file, chosen from default values, entered manually, etc. Ultimately, the user interface will allow a user to instruct the computer 30 to perform a test run on a device under test (step 72).

Figure 4:
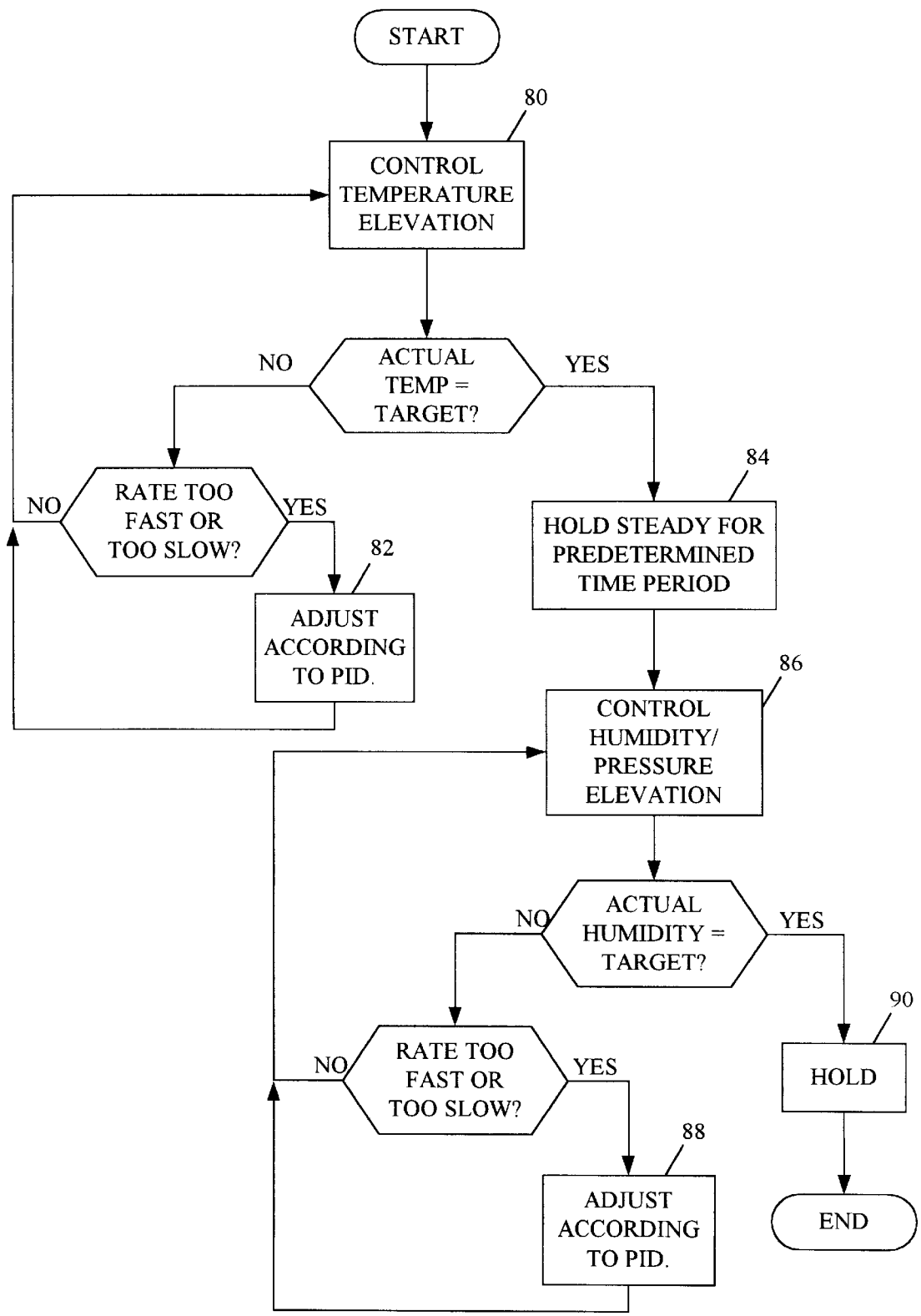
FIG. 4 is a flowchart illustrating the operation of an environmental test chamber constructed in accordance with the preferred embodiment of the invention.

In this regard, references made to FIG. 4, which is a software flow chart illustrating the top-level operation of a test run, in accordance with the concepts of the present invention. As been previously discussed, the goal of the present invention is to control the environment within a test chamber 12 of an environmental test apparatus to minimize (if not eliminate) the formation of condensation within the chamber and on the device under test. In this regard, it has been determined that when temperature and humidity levels are elevated similanteously, condensation within the test chamber is more prevalent. Accordingly, the preferred embodiment of the present invention operates to first controllably elevate the temperature within the test chamber (step 80). During this temperature elevation process, the preferred embodiment may also verify that the rate at which the temperature is changing is occurring at a certain pre-defined gradient. This gradient may be defined by the testing procedure or otherwise. Significant for purposes of the preferred embodiment, if the temperature elevation is occurring either too fast, or too slow, the on-off duty cycle of the air heater may be adjusted in accordance with a control algorithm, such as a PID (step 82). Once the target temperature inside the temperature inside the chamber has been reached, the invention operates to stabilize the air temperature within the test environment at or near that the target temperature for a predetermined period of time (step 84). This predetermined period of time may vary based upon a number of factors including the amount that the temperature has been elevated, the rate at which the temperature was elevated, and/or other factors. Thereafter, the invention operates to controllably elevate the humidity and/or atmospheric pressure levels within the test chamber (step 86).

As with the temperature elevation routine, during this humidity elevation process, they preferred embodiment monitors the humidity and/or atmosphere pressure gradient to determine that it does not exceed certain predefined boundaries. If so, then the operation of the fluid heater may be adjusted in accordance with a PID algorithm (step 88) in order vary the humidity gradient, so that controlled humidity/pressure elevation within the test chambers is achieved. Finally, once the environmental test chamber has reached its target temperature and humidity it is stabilized at or near those target levels for a specified period of time in order to test the operation of the device under test at that predefined environmental condition (step 90).

The foregoing description has been presented for purposes of illustration and description. It is not intended to be exhaustive or to limit the invention to the precise forms disclosed. Obvious modifications or variations are possible in light of the above teachings. The embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. An apparatus for performing environmental testing on a device comprising:
   a test chamber;
   at least one air heater for controlling air temperature within the test chamber;
   at least one liquid heater for disposed in connection with a liquid reservoir for heating the liquid to control humidity within the test chamber;
   a first controller configured to control the at least one air heater;
   a second controller configured to control the at least one liquid heater; and
   a computer for providing centralized and independent control of both the first controller and the second controller, wherein the computer is configured to control the first controller to elevate the temperature of the test chamber, then control the first controller to stabilize the temperature of the test chamber, then control the second controller to elevate the humidity within the test chamber.

2. The apparatus as defined in claim 1, wherein the computer is configured to control the first controller to hold the temperature within the test chamber at a substantially constant value, while controlling the second controller to elevate the humidity within the test chamber.

3. The apparatus as defined in claim 1, wherein the computer is configured to control the second controller so as to hold the humidity within the test chamber at a substantially constant value, while controlling the first controller to elevate the temperature of the test chamber.

4. The apparatus as defined in claim 1, wherein the computer is a microprocessor-based computer.

5. The apparatus as defined in claim 1, wherein the first controller includes at least one relay for controlling the operation of the at least one air heater.

6. The apparatus as defined in claim 1, wherein the second controller includes at least one relay for controlling the operation of the at least one liquid heater.

7. An apparatus for performing environmental testing on a device comprising:

a test chamber;

first means for controlling air temperature within the test chamber;

second means for controlling the humidity within the test chamber;

first control means for controlling the first means;

second control means for independently controlling the second means; and coordinating means for coordinating the independent control of the first control means and the second control means.

8. The apparatus as defined in claim 7, wherein the first means includes at least one air heater.

9. The apparatus as defined in claim 7, wherein the second means includes at least one fluid heater.

10. The apparatus as defined in claim 7, wherein the means includes a computer executing program code to control the operation of the first and second means.

11. The apparatus as defined in claim 7, wherein the coordinating means is configured to control the first control means and second control means so that the air temperature within the test chamber is held at a substantially constant level when the humidity within the test chamber is being controlled to change at a substantial rate.

12. The apparatus as defined in claim 7, wherein the coordinating means is configured to control the first control means and second control means so that the humidity within the test chamber is held at a substantially constant level when the air temperature within the test chamber is being controlled to change at a substantial rate.

\* \* \* \* \*